(12) United States Patent
Kimmel et al.

(10) Patent No.: US 8,790,362 B1
(45) Date of Patent: Jul. 29, 2014

(54) CATHETER FOR POSITIONING A LEAD IN THE VASCULATURE

(75) Inventors: Scott Kimmel, St. Paul, MN (US); Chris Colway, Saint Louis Park, MN (US); Brian Pedersen, East Bethel, MN (US); Elliot Bridgeman, Big Lake, MN (US); Kevin Pietsch, Greenfield, MN (US)

(73) Assignee: Greatbatch Ltd., Clarence, NY (US)

( * ) Notice: Subject to any disclaimer, the term of this patent is extended or adjusted under 35 U.S.C. 154(b) by 222 days.

(21) Appl. No.: 13/185,054

(22) Filed: Jul. 18, 2011

Related U.S. Application Data

(60) Provisional application No. 61/365,012, filed on Jul. 16, 2010, provisional application No. 61/505,575, filed on Jul. 8, 2011.

(51) Int. Cl.
*A61B 17/32* (2006.01)

(52) U.S. Cl.
USPC .............................. 606/180; 606/170; 600/564

(58) Field of Classification Search
USPC ................. 606/129, 167, 159, 180, 184, 170; 600/562, 564, 566, 567
See application file for complete search history.

(56) References Cited

U.S. PATENT DOCUMENTS

| | | | |
|---|---|---|---|
| 5,328,467 A | | 7/1994 | Edwards et al. |
| 5,776,142 A * | | 7/1998 | Gunderson ................... 623/1.11 |
| 6,258,111 B1 * | | 7/2001 | Ross et al. ..................... 606/171 |
| 6,752,800 B1 | | 6/2004 | Winston et al. |
| 7,096,071 B2 | | 8/2006 | Ollivier et al. |
| 7,544,197 B2 | | 6/2009 | Kelsch et al. |
| 7,682,358 B2 | | 3/2010 | Gullickson et al. |
| 7,819,819 B2 * | | 10/2010 | Quick et al. ................... 600/564 |
| 2005/0165345 A1 * | | 7/2005 | Laufer et al. ..................... 604/26 |
| 2007/0179473 A1 | | 8/2007 | Masters et al. |
| 2007/0232981 A1 * | | 10/2007 | Ravenscroft et al. ........ 604/6.16 |
| 2009/0287203 A1 | | 11/2009 | Mazzone et al. |
| 2010/0324446 A1 * | | 12/2010 | Pendleton ..................... 600/565 |

* cited by examiner

*Primary Examiner* — Katherine Dowe
*Assistant Examiner* — Sidharth Kapoor
(74) *Attorney, Agent, or Firm* — Michael F. Scalise

(57) ABSTRACT

A novel catheter is described. The catheter comprises a handle, an inner sheath providing an inner sheath lumen extending along a first length from a proximal inner sheath portion supported by the handle to a distal inner sheath portion connected to a cage gripper, and an outer sheath having a second length extending from a proximal outer sheath portion supported by the handle to a distal outer sheath portion connected to a cage housing. The inner sheath rotatably resides inside the outer sheath with the cage gripper rotatably housed inside cage housing. During a surgical procedure, a distal bridge portion of the inner sheath is connected to an opening in the lead sidewall with the lead received inside the cage housing. A gear knob is manipulated to cause the inner sheath to rotate with respect to the outer sheath so that the cage gripper is moved from an un-deployed position housed inside the cage gripper to a deployed position completely surrounding the lead connected to the distal bride. The catheter connected to the lead is moved into and to a desired location in a vasculature. Then, a screw driver is inserted through the housing and inner sheath lumens and into the lead and manipulated to screw the distal electrode into body tissue. Manipulating the gear knob causes the inner sheath to rotate the cage gripper from the deployed to the un-deployed position and then the catheter is separated from the lead and removed from the vasculature, leaving the lead behind.

20 Claims, 17 Drawing Sheets

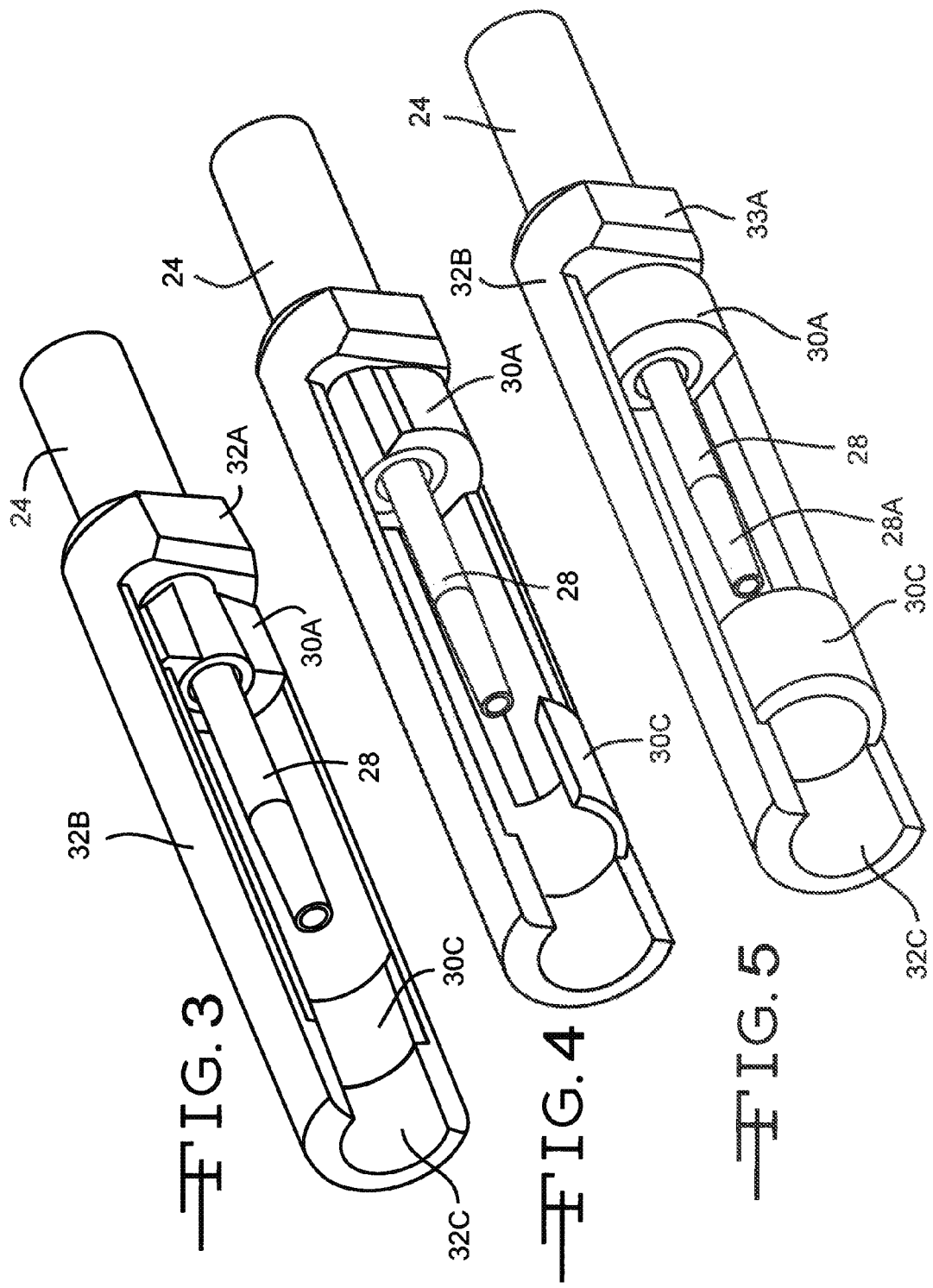

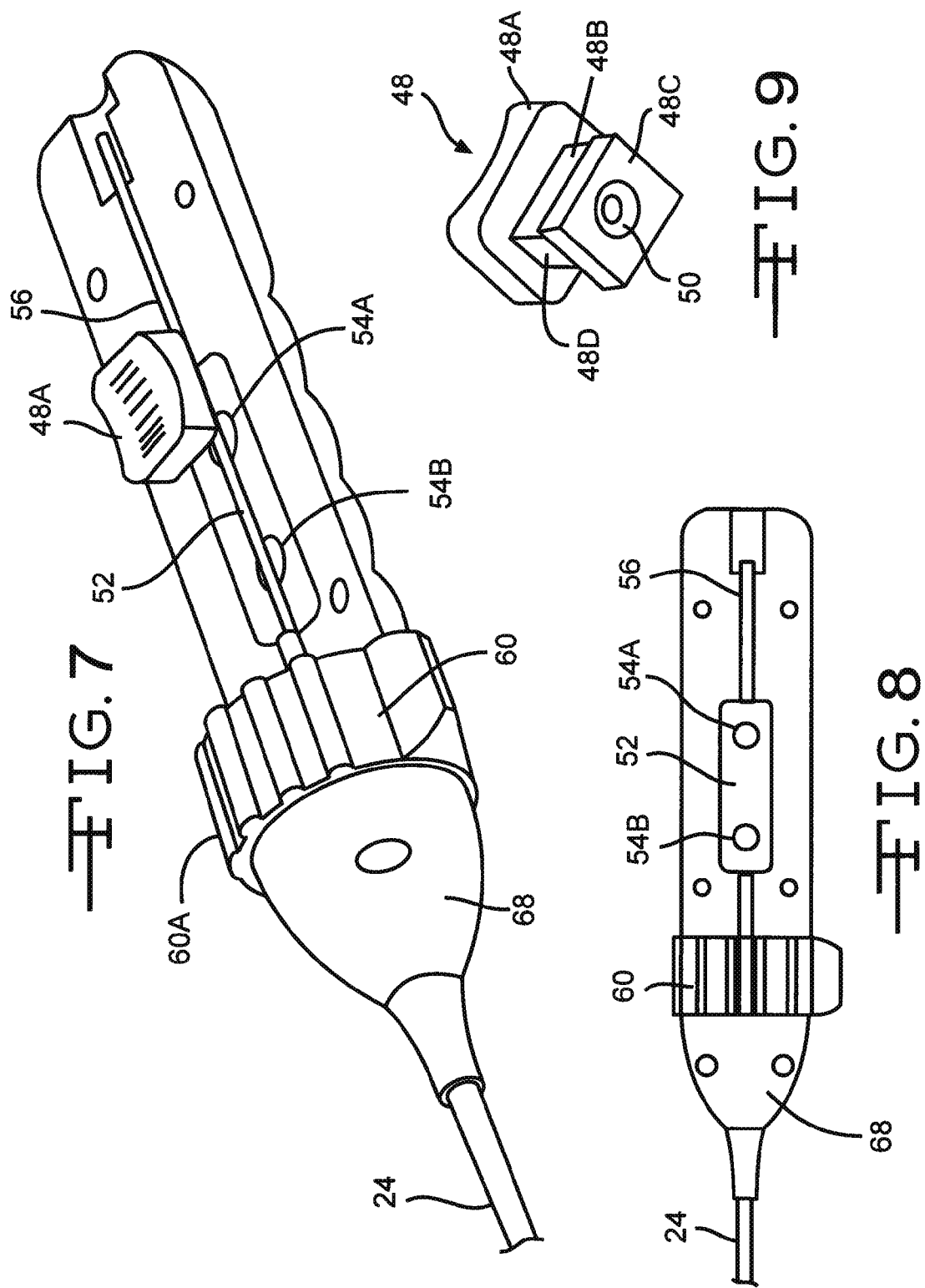

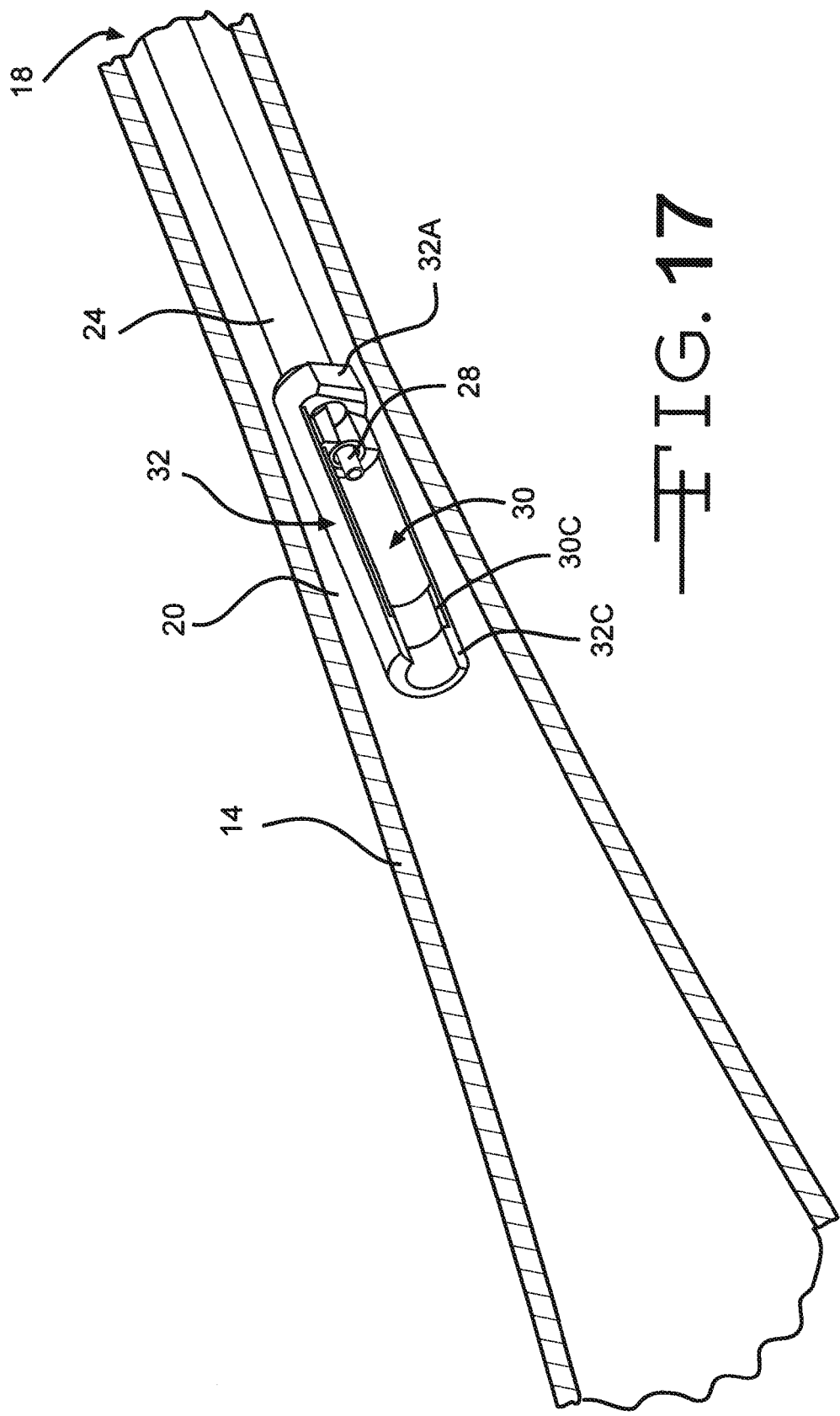

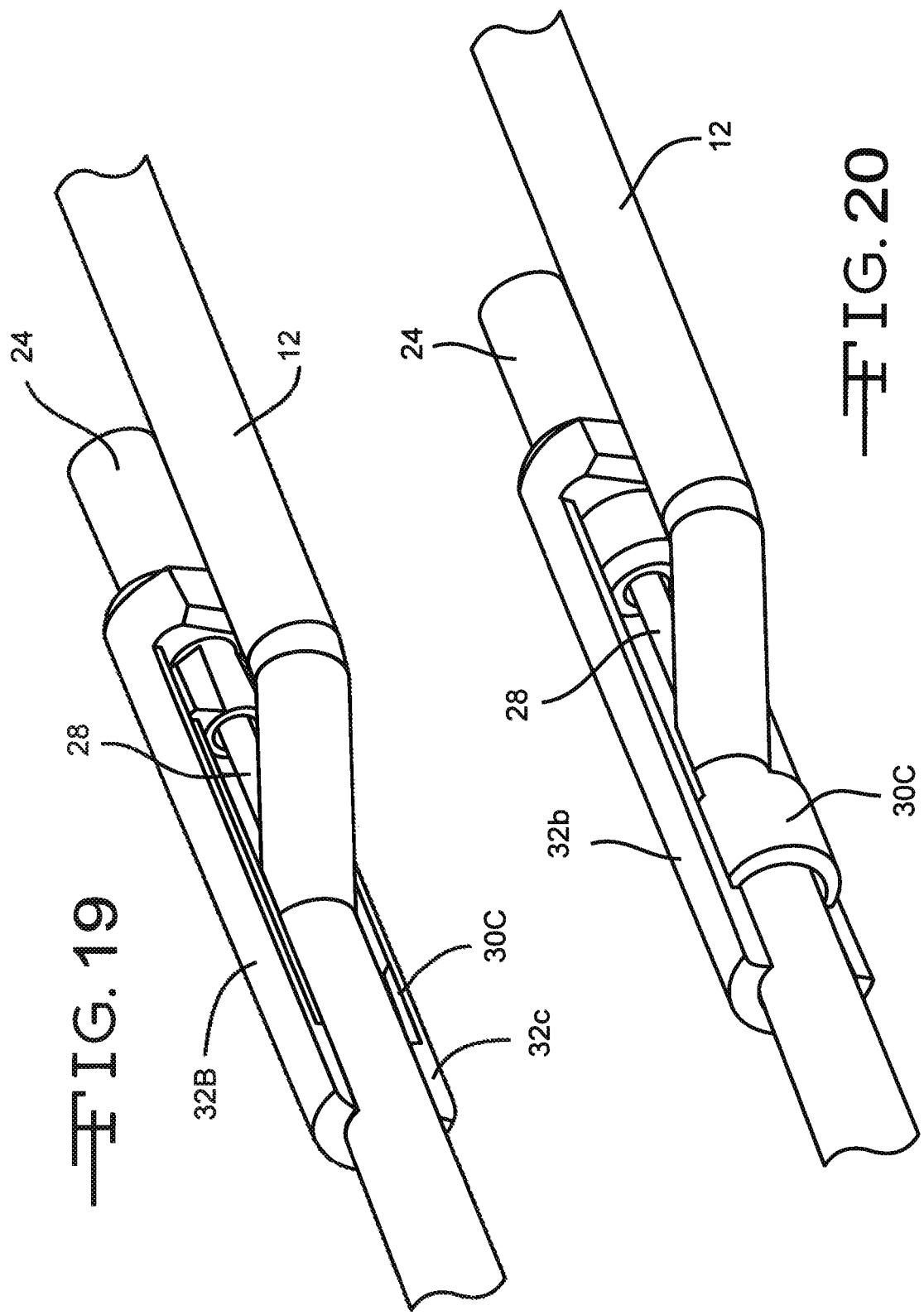

CATHETER FOR POSITIONING A LEAD IN THE VASCULATURE

CROSS-REFERENCE TO RELATED APPLICATIONS

The present application claims priority from U.S. Provisional Application Ser. Nos. 61/365,012, filed Jul. 16, 2010 and 61/505,575, filed Jul. 8, 2011.

BACKGROUND OF THE INVENTION

The present invention is related generally to catheters for accessing the human or animal vasculature. More particularly, the invention describes a catheter that is adapted to position a lead in a vasculature, for example, to anchor a lead electrode in the apex of the right ventricle.

SUMMARY OF THE INVENTION

Sudden cardiac death remains a major threat despite advances in medication and other treatments for preventing recurrent heart attacks and heart failure. Each year, it claims the lives of more than 400,000 Americans alone, and the overwhelming majority of those deaths are caused by ventricular fibrillation, or rapid, uncoordinated contractions.

Randomized trials have shown that implantable defibrillators dramatically reduce mortality in patients with a history of arrhythmias, or abnormal heart rhythms caused by ventricular fibrillation, or in patients at risk for sudden cardiac death. Today, the patient population of defibrillator candidates is significantly underserved. Without a defibrillator, a victim of sudden cardiac arrest has only a five-percent chance of survival. Implantable defibrillators currently on the market, however, are similar in form and function: titanium boxes implanted in the pectoral region. In most patients, this device creates a "cardiac bump" that is visible when not covered by loose-fitting clothes. The implant procedure typically requires hospitalization, followed by frequent device adjustments of complex features that few have the time or requisite skills to fully interpret or optimize.

As a solution, InnerPulse, Inc. has developed a percutaneous implantable cardioverter defibrillator. The PICD™ device is implanted within the patient's vascular system using the present catheter.

SUMMARY OF THE INVENTION

The present invention relates to a catheter comprising a handle; an inner sheath providing an inner sheath lumen extending along a first length from a proximal inner sheath portion supported by the handle to a distal inner sheath portion connected to a cage gripper; and an outer sheath having a second length extending from a proximal outer sheath portion supported by the handle to a distal outer sheath portion connected to a cage housing, wherein at least a portion of the inner sheath rotatably resides inside the outer sheath with the cage gripper rotatably housed inside cage housing. The handle provides a handle lumen in open communication with the inner sheath lumen. The housing supports a first gear means connected to the inner sheath, the first gear means being manipulatable to rotate the inner sheath inside the outer sheath to consequently rotate the cage gripper inside the cage housing between a closed, un-deployed position to an open, deployed position. The first gear means comprises a rotatable gear knob that meshes with a sun gear connected to the proximal inner sheath portion for selectively rotating the inner sheath inside the outer sheath. Further, the sun gear supports spaced apart first and second magnets that are selectively attractable to a third magnet supported by the handle to thereby maintain the cage gripper connected to the inner sheath in either the un-deployed or the deployed position. That way, the gear knob and the sun gear provide a gear ratio such that angular manipulation of the gear knob produces a greater angular movement of the sun gear.

Moreover, the handle supports a valve that is in communication with the handle lumen and the inner sheath lumen.

The handle also supports an actuator button connected to a flexible tubing portion of the lumen. The actuator button is movable longitudinally along the handle from a first position in which the flexible tubing is relatively straight for unobstructed communication from the valve and the handle lumen and into the inner sheath lumen to a second position in which the flexible tubing is kinked to thereby block unobstructed communication through the handle lumen. The actuator button supports spaced apart fourth and fifth magnets that are selectively attractable to a sixth magnet supported by the handle to thereby maintain the flexible tubing connected to the actuator button in either the straight or the kinked configuration.

A method for implanting the electrode of a lead into body tissue using the present catheter is also described. The lead has a sidewall of a length extending from a distal electrode to a proximal portion connectable to a medical device. A distal bridge portion of the inner sheath is connected to an opening in the lead sidewall with the lead received inside the cage housing. A gear knob is manipulated to cause the inner sheath to rotate with respect to the outer sheath so that the cage gripper is moved from an un-deployed position housed inside the cage gripper to a deployed position surrounding the lead connected to the distal bride. The catheter connected to the lead is moved into and to a desired location in a vasculature. Then, a screw driver is inserted through the housing and inner sheath lumens and into the lead and manipulated to screw the distal electrode into body tissue. Manipulating the gear knob causes the inner sheath to rotate the cage gripper from the deployed to the un-deployed position and then the catheter is separated from the lead and removed from the vasculature, leaving the lead behind.

The foregoing and additional advances and characterizing features of the present invention will become clearly apparent upon reading the ensuing description together with the included drawings wherein:

BRIEF DESCRIPTION OF THE DRAWINGS

FIG. 3 is a perspective view showing the cage assembly 20 with the cage gripper 30 in an un-deployed position, completely housing inside the case housing 32.

FIG. 4 is a perspective view of the cage assembly 20 shown in FIG. 2 with the cage gripper 30 partially rotated inside the cage housing 32 supported at the distal end of an outer sheath 24 with an inner sheath (not shown) supporting a lead bridge 28 disposed inside the cage housing.

FIG. 5 is a perspective view showing the lead bridge 28 housed inside the cage assembly 20 shown in FIG. 3 with the cage gripper 30 having been rotated inside the cage housing 32 to a fully deployed position.

FIG. 7 is a perspective view of the handle assembly 16 shown in FIG. 6 partly broken away to illustrate the actuator button 48 in relation to the proximal and distal magnets 54A, 54B supported by a land 52 inside the handle assembly 16.

FIG. 8 is a plan view of a land 52 supporting the proximal and distal magnets 54A, 54B inside the handle assembly 16.

FIG. 9 is a perspective view of the actuator button 48.

FIG. 17 is a perspective view showing the cage assembly 20 at the distal end of the sheath assembly 18 being moved through a vasculature 14.

FIG. 19 is a perspective view showing the cage assembly 20 engaged with the lead 12 illustrated in FIG. 18 and with the gripper finger 30C in an un-deployed position shown in FIG. 3.

FIG. 20 is a perspective view showing the cage assembly 20 engaged with the lead 12 illustrated in FIG. 19, but with the gripper finger 30C having been rotated to the fully deployed position shown in FIG. 5.

DETAILED DESCRIPTION OF THE PREFERRED EMBODIMENTS

Figure 1:
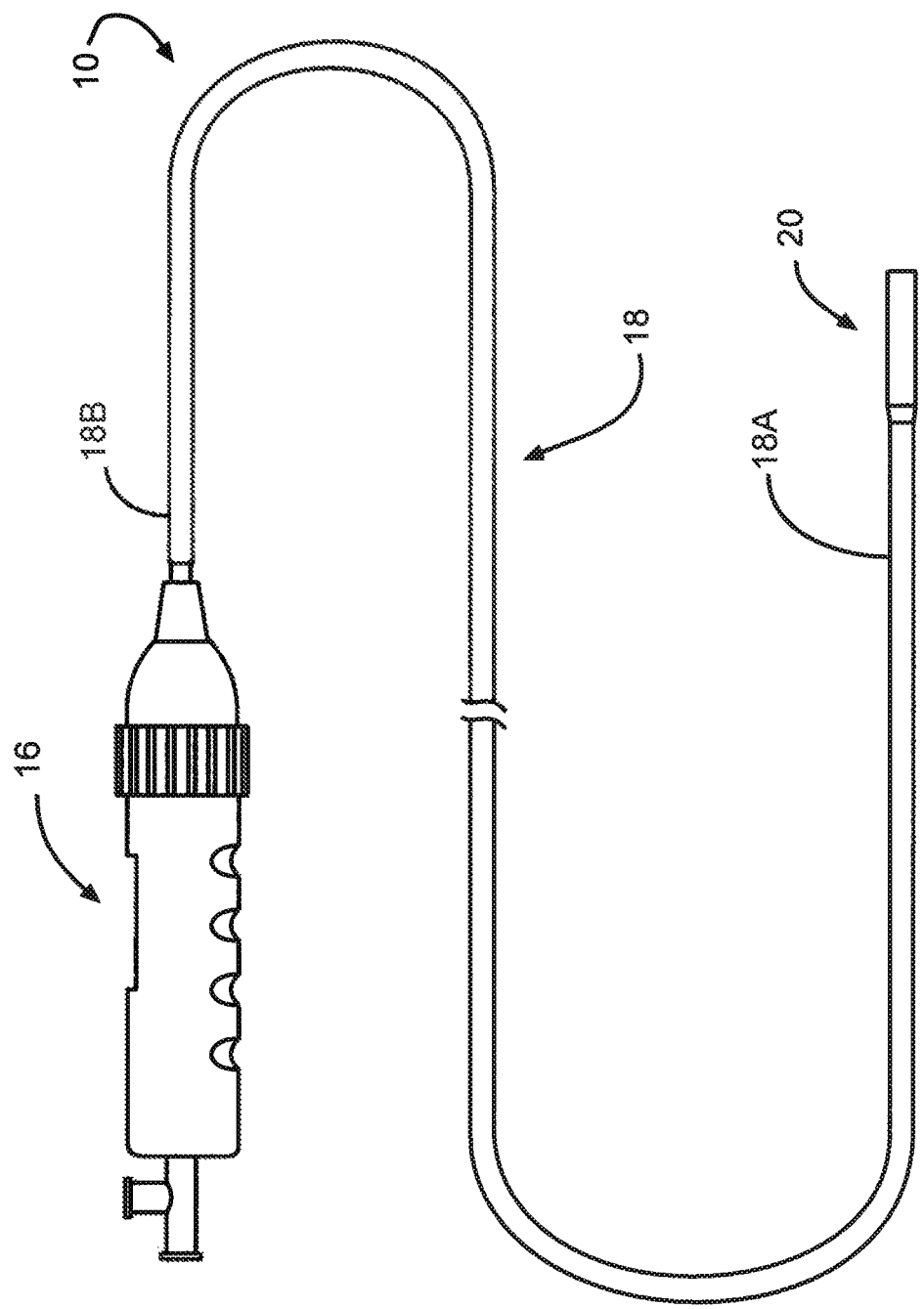
FIG. 1 is a schematic view of the catheter 10 of the present invention.
Figure 2:
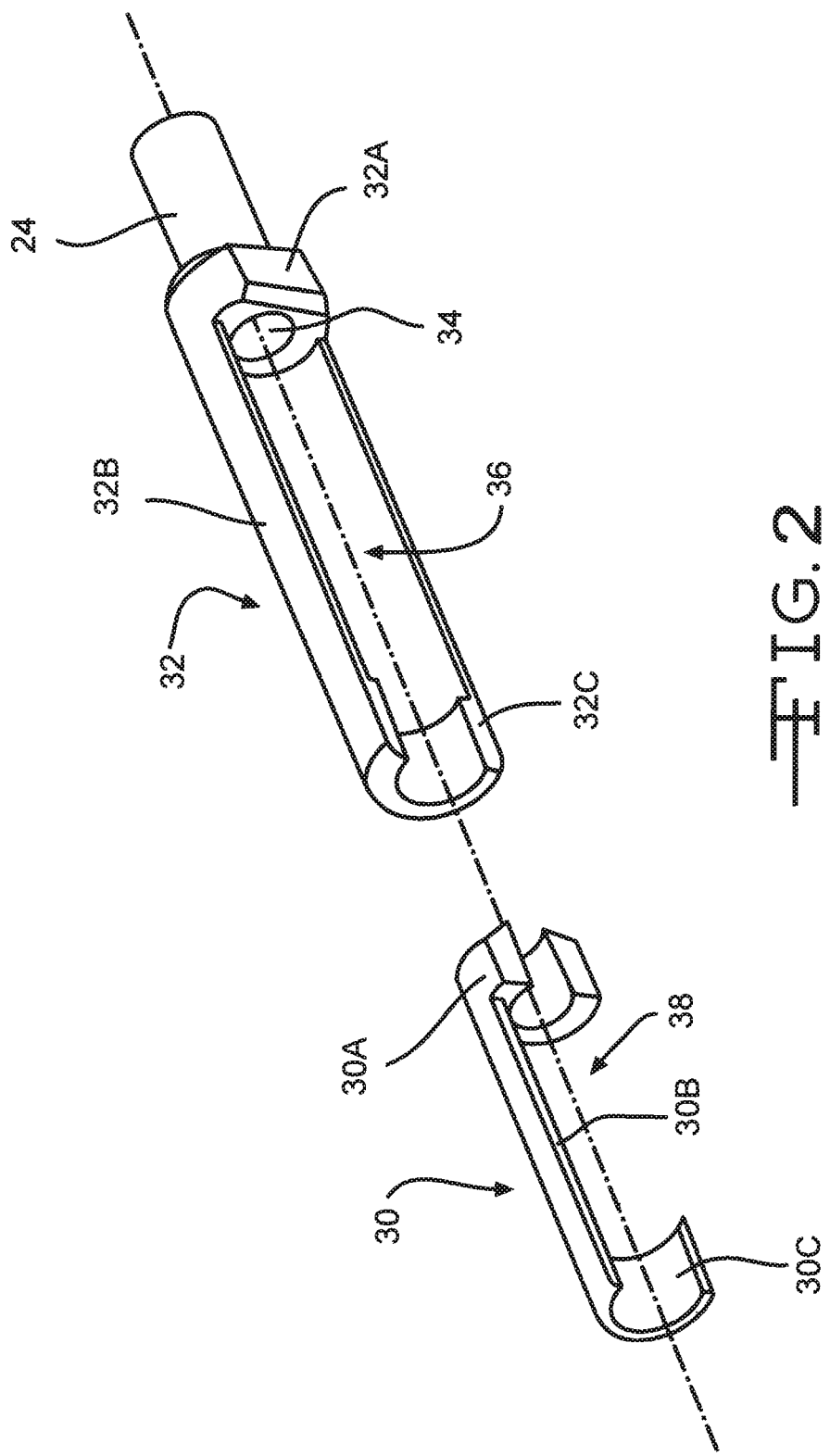
FIG. 2 is a perspective view of cage gripper 30 separated from a cage housing 32, together comprising a cage assembly 20 of the present catheter 10.

Turning now to the drawings, FIG. 1 illustrates a catheter 10 according to the present invention. The catheter 10 is useful for anchoring a lead 12 (FIGS. 18 to 20) in a desired position in a vasculature 14 (FIGS. 17 and 17A) and comprises a handle assembly 16 supporting a flexible sheath assembly 18. The sheath assembly 18, in turn, supports a cage assembly 20. The vasculature 14 can be that of a human or an animal.

Figure 11:
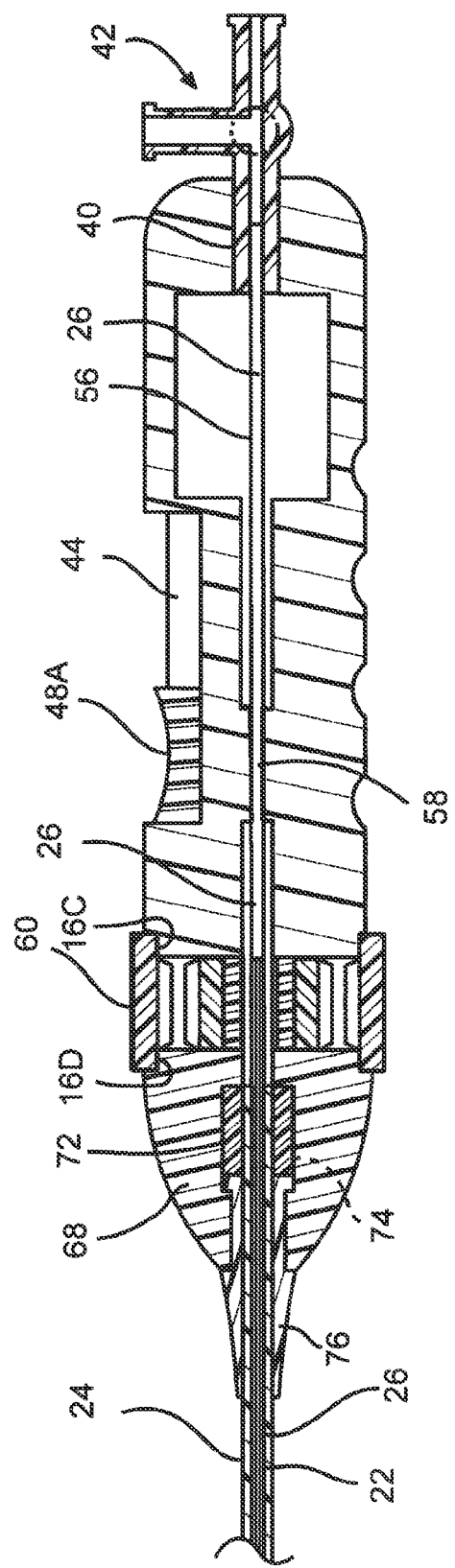
FIG. 11 is a side cross-sectional view of the handle assembly 16 having the actuator button 48 in its proximal position with the flexible tubing 56 being unkinked.
Figure 12:
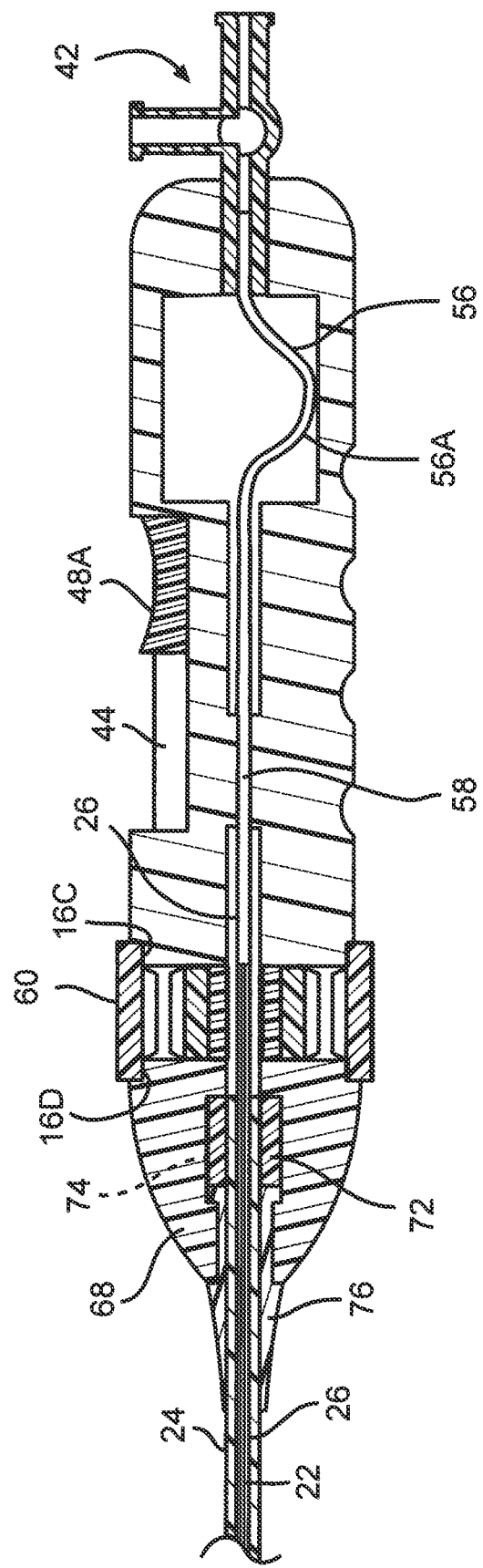
FIG. 12 is a side cross-sectional view of the handle assembly 16 shown in FIG. 11 having the actuator button 48 in its proximal position with the flexible tubing 56 kinked.
Figure 13:
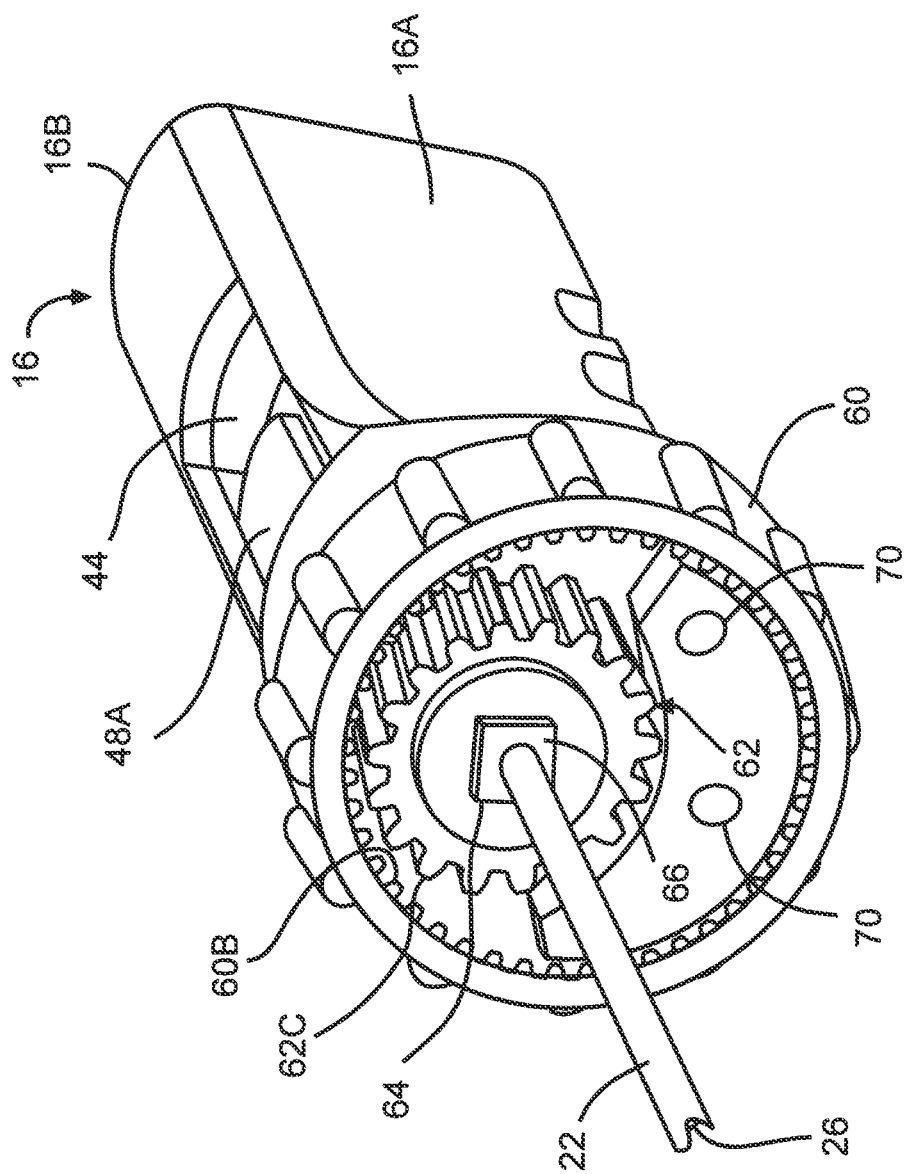
FIG. 13 is a perspective view showing how the gear teeth 60B of the rotatable knob 60 mesh with a sun gear 62 supporting the inner sheath 22.

As shown in FIGS. 11 and 12, the sheath assembly 18 comprises an inner sheath 22 disposed inside an outer sheath 24, both being elongate tubular structures that are flexible yet substantially non-compressible along their lengths. A distal end 18A (FIG. 1) of the sheath assembly supports the cage assembly 20 while a proximal sheath portion 18B connects to the handle assembly 16.

An exemplary construction for the sheath assembly 18 comprises the outer tubular sheath 24 formed of a polymeric material, such as PEBAX, encasing a tubular wire (not shown) braided as a mesh. The inner tubular sheath 22 is of a second polymeric material, for example PTFE, and resides inside the PEBAX outer tubular sheath 24. The inner sheath 22 provides part of a lumen 26 (FIGS. 11 to 14) extending from the handle assembly 16 to a lead bridge 28 (FIGS. 3 to 5, 17, 17A, 18 to 21, 23 and 25) supported at the distal end thereof. PTFE material provides the inner tubular sheath 22 with sufficient lubricity so that medical instruments, fluids, and the like, can readily slide through its lumen 26 while the inner sheath is selectively rotatable inside the outer sheath 24 using a minimal amount of force. The outer sheath 24 has sufficient lubricity to be relatively easily pushed or moved through the vasculature 14. Rotational movement of the inner sheath 22 inside the outer sheath 24 will be described in detail hereinafter.

As shown in FIGS. 2 to 5, the cage assembly 20 supported at the distal ends of the inner and outer sheaths 22, 24 comprises a cage gripper 30 rotatably housed inside a cage housing 32.

The cage housing 32 comprises a sidewall extending from an outer base 32A supported at the distal end of the outer sheath 24 in a fluid tight relationship. The outer base 32A in turn supports a partially cylindrically-shaped portion 32B having a first length extending to a distal end 32C thereof. A longitudinal bore 34 is provided in the base 32A. A lateral opening 36 extends along the length of the partially cylindrical portion 32B from the outer base 32A and its bore 34 to and through the distal end 32C of the cage housing 32.

The cage gripper 30 resides inside the cage housing 32 and comprises an inner base 30A supported at the distal end of the inner sheath 22 in a fluid tight engagement. The inner base portion 30A of the cage gripper 30 supports a partially cylindrically-shaped portion having a length extending along an intermediate gripper portion 30B to a distal annularly-shaped gripper finger 30C. An inner lateral opening 38 extends along a second length of the intermediate portion 30B and the distal gripper finger 30C. However, the intermediate portion 30B has a lesser annular extent than the gripper finger 30C. This means that the inner lateral opening 38 has a greater annular extent in the vicinity of the intermediate portion 30B than at the distal gripper finger 30C. With the cage gripper 30 residing inside the cage housing 32, the first and second openings 36, 38 align with each other.

Figure 6:
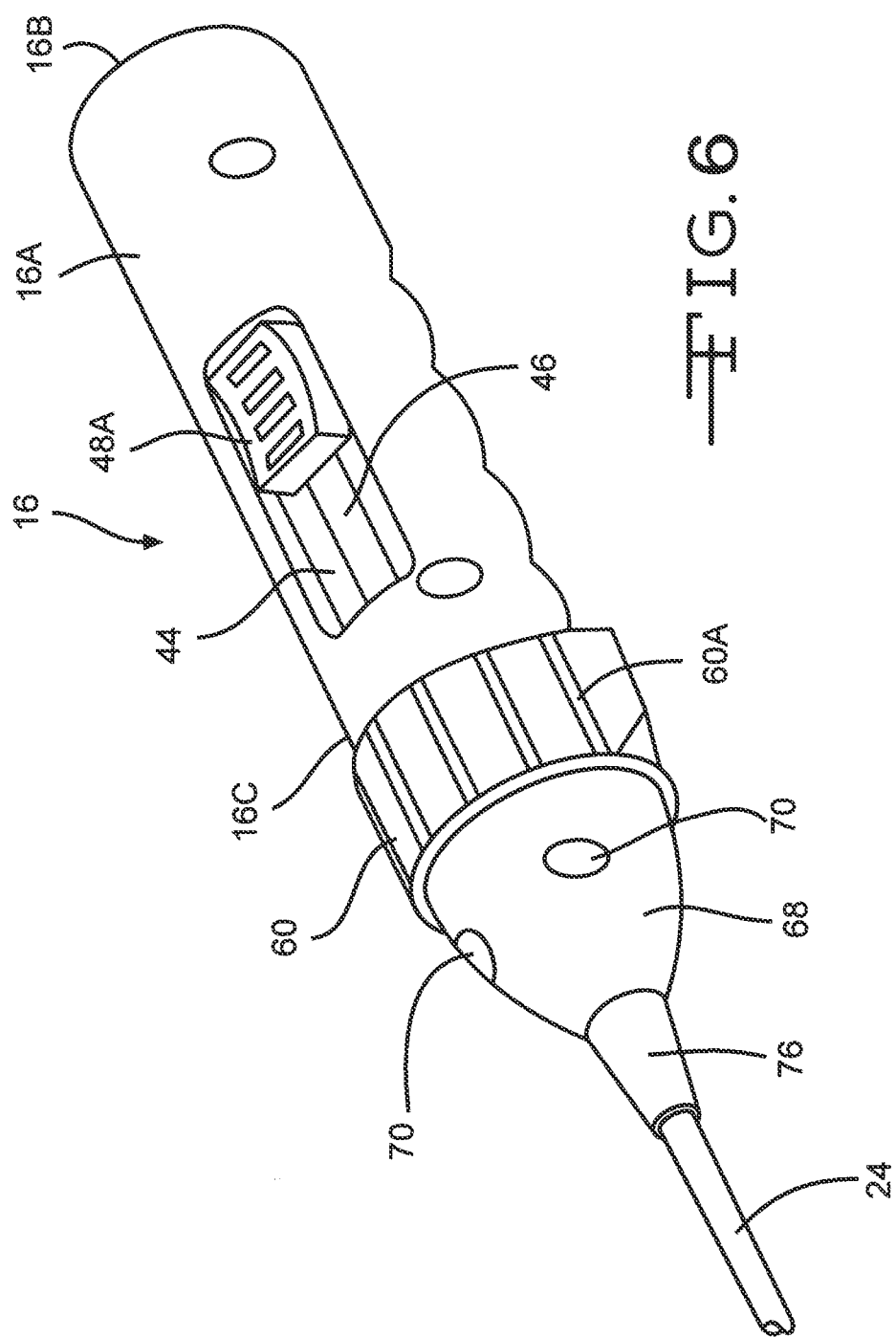
FIG. 6 is a perspective view of the handle assembly 16.
Figure 10:
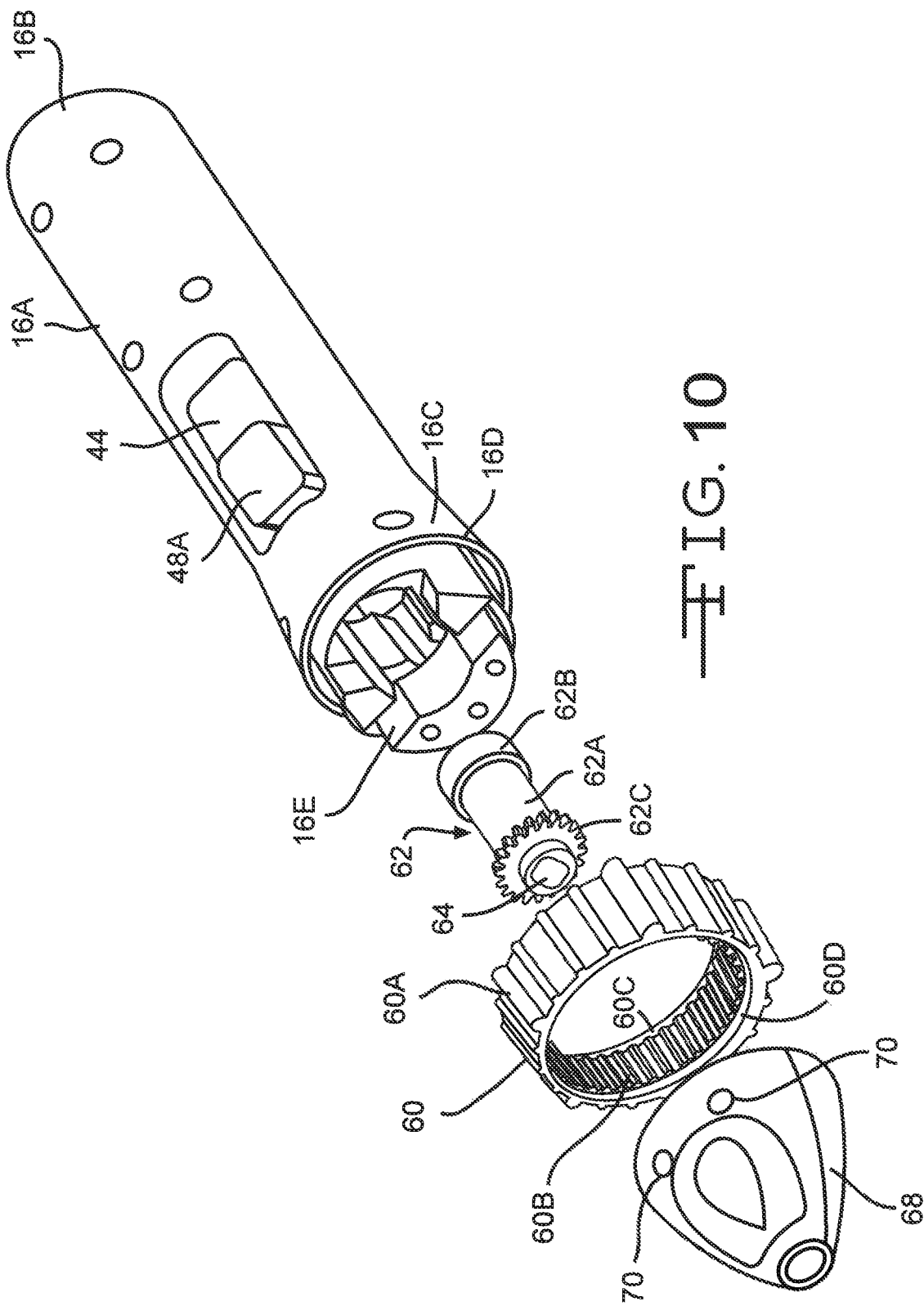
FIG. 10 is a partially exploded, perspective view of the handle assembly 16.

One embodiment of the handle assembly 16 (FIG. 1) includes a right handle portion (not shown) mated to a left handle portion (not shown). In another embodiment, the handle assembly 16 comprises upper and lower portions that are mated to each other. In any event, the handle halves are mirror images of each other and provide an ergonomically designed curved shape, the extent of which is defined by an annular sidewall 16A extending longitudinally from a proximal end 16B to a distal or forward end 16C (FIG. 6). The proximal end 16B includes an opening 40 supporting a 3-way valve 42 (FIGS. 11 and 12).

A rectangularly-shaped recess 44 leading to a slot 46 of a reduced width is provided part-way into the handle from an upper surface thereof. The recess 44 and slot 46 extend along the length of the handle 16, aligned with its longitudinal axis. An actuator button 48 (FIGS. 7 and 9) comprises a thumb plate 48A supported on a vertically aligned post 48B connected to a base plate 48C. The thumb plate 48A is sized to move back and forth along the recess 44 with the vertical post 48B confined along the slot 46. The base plate 48C supports a first magnet 50 disposed inside the handle.

As shown in FIGS. 7 and 8, an internal land 52 inside the handle 16 supports a proximal magnet 54A spaced from a longitudinally aligned distal magnet 54B. The handle post 48B further supports a relatively short piece of flexible tubing 56, for example, of TYGON®. The TYGON® tubing 56 provides a robust portion of the lumen 26 that is highly resistant to scuffing, scratching and tearing, but which kinks fairly easily while recovering its inner circular lumen shape upon straightening. Therefore, it is ideal for an application in which one wants the lumen to collapse and open repeatedly and reliably.

A tubing bridge 58 supported by the opposed, distal face 48D of the post 48 (FIG. 9) connects between the inner sheath 22 and the flexible tubing 56. A suitable material for the tubing bridge 58 is PETROTHENE®. The lead bridge 28 is an extruded tubular portion of the inner sheath. Together, the inner sheath 22 including the flexible tubing 56, the tubing bridge 58 and the lead bridge 28 are about 35 inches long. It has an inner diameter of about 0.044 inches and an outer diameter of about 0.077 inches. A tip 12A (FIG. 5) of the lead bridge 28 is thermoformed with a taper angle of about 4° to 6°.

As previously described, the inner sheath 22 is part of the sheath assembly 18 and provides part of the lumen 26 extending to the cage assembly 20. The actuator button 48 provides open communication along the lumen 26 from the 3-way valve 42, the vertical post 48B of the actuator button, the flexible tube 56, the tubing bridge 58 and into the inner sheath 22 including the distal bridge 28.

As shown in FIG. 12, when the actuator button 48 is in its proximal position, held there by attraction of the first button magnet 50 with the proximal handle magnet 54A, the flexible tube 56 has a kink 56A that prevents movement of a stylet (not shown), and the like, into the lumen 26 including the inner sheath 22. When the actuator button 48 is moved to its distal position, held there by attraction between the button magnet 50 and the distal magnet 54B, the flexible tube 56 is un-kinked and relatively straight to permit communication through the 3-way valve 42 and into the lumen 26 through the flexible tube 56, the vertical post 48B, the tubing bridge 58 and into the inner sheath 22 and finally the distal bridge 28.

Using magnets 54A, 54B for stops imparts a smooth feel for transitioning the actuator button 48 distally and proximally between the forward and backward positions. Moreover, this magnetic actuation does not require the user to depress the button 48 as much as, for example, is typically required of a spring loaded button (not shown). Spring loaded buttons are often standard on catheter handles containing slider buttons. The force induced by the magnets 50 and 54A, 54B is also robust and repeatable, and less susceptible to material changes that can be induced by standard accelerated shelf life testing and sterilization.

As shown in FIGS. 6 and 10 to 12, the forward end 16C of the handle assembly 16 provides an annular handle ledge 16D of a reduced diameter that rotatably supports a knob 60. The knob 60 is provided with a series of raised fins 60A between which a user can fit his thumb for rotational manipulation thereof. The knob 60 further comprises an annular inner gear 60B disposed between internal proximal and distal bearing surfaces 60C and 60D, respectively.

Figure 15:
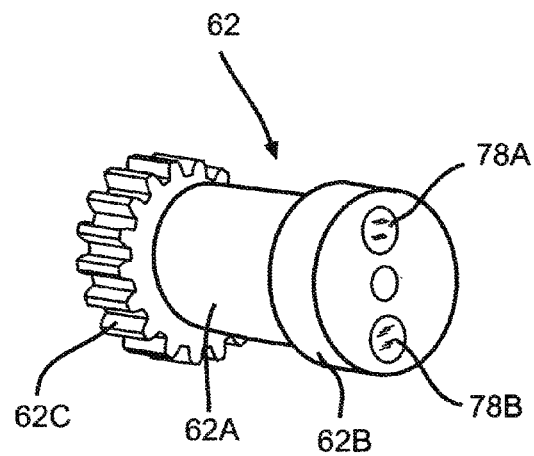
FIG. 15 is a cross-sectional view in perspective of the sun gear 62 supporting magnets 78A, 78B.
Figure 16:
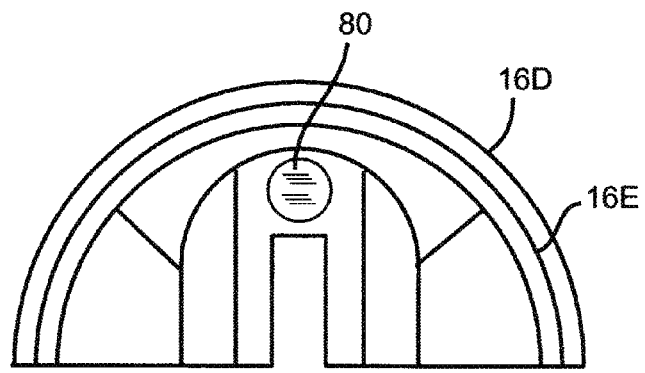
FIG. 16 is a schematic view showing the housing 16 supporting a magnet 80 that is selectively attracted to the magnets 78A, 78B of the sun gear 62.

A sun gear 62 (FIGS. 10 and 15) is an elongate member comprising an annular bearing surface 62A disposed between a proximal enlarged annular portion 62B and distal gear teeth 62C. A rectangularly-shaped nest 64 is provided in the distal end of the sun gear 62 surrounded by the annular gear teeth 62C.

As shown in FIGS. 11 to 14, the inner sheath 22 supports an overmolded tab 66 at its proximal end that fits snuggly into the nest 64 provided in the sun gear 62. The sun gear 62 is rotatably supported by a platform 16E extending outwardly from the proximal end of the handle 16. The inner gear 60B of the knob 60 meshes with the gear teeth 62C of the sun gear 62. That way, manipulation of the knob 60 causes the knob to rotate on the annular handle ledge 16D as the meshed sun gear 62 rotates the tab 66 and the inner sheath 22.

Figure 14:
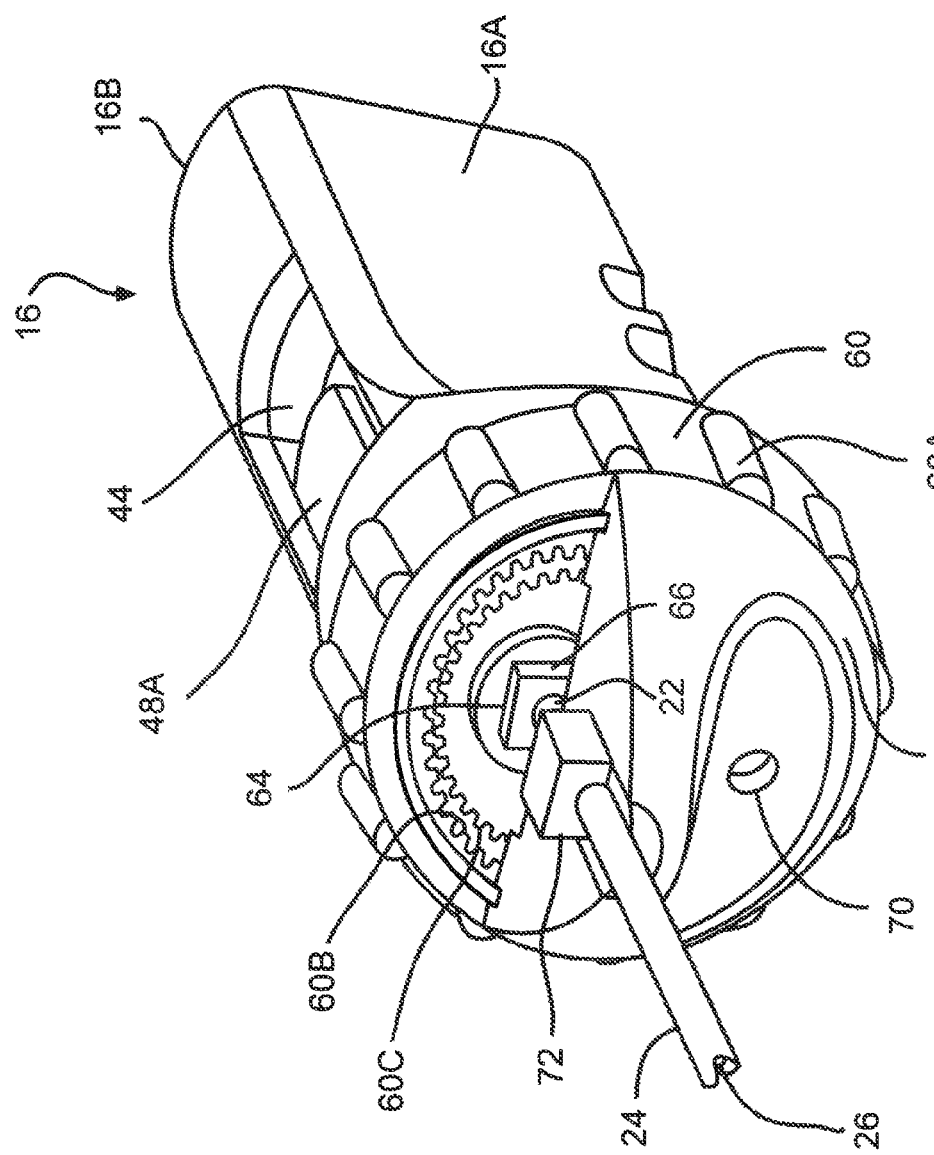
FIG. 14 is a perspective view showing the gear teeth 60B of the rotatable knob 60 meshed with a sun gear 62 and a nose cone 68 supporting the outer sheath 24.

A nose cone 68 extends forwardly or distally, supported by the internal distal bearing surface 60D of the knob 60. A number of screw openings 70 receive threaded members (not shown) connecting between the nose cone 68, the intermediate knob 60 and the handle assembly 16. In a similar manner as the tab 66 received in the nest 64 of the sun gear 62, a second tab 72 is overmolded onto the proximal end of the outer sheath 24. As shown in FIGS. 11, 12 and 14, this tab 72 is snuggly received in a nest 74 in the nose cone 68. That way, the outer sheath 24 is fixed in relation to the handle assembly 16 as the knob 60 is rotated with respect to the handle to thereby rotate the inner sheath 22 inside the stationary outer sheath. A strain relief cone 76 supported at the distal end of the nose cone 68 provides additional support to the outer sheath 24 at the handle assembly 16.

In that manner, rotational movement of the knob 60 on the handle ledge 16D rotates the gear teeth 60B meshed with the sun gear 62 and its nested tab 66 fixedly supported on the proximal end of the inner sheath 22. In this manner, rotational manipulation of the knob 60 causes the inner sheath 22 to rotate inside the outer sheath 24. Moreover, rotation of the inner sheath 22 causes rotational movement of the cage gripper 30 inside the cage housing 32.

Since the cage assembly 20 has only the open or deployed (FIG. 3) and closed or un-deployed (FIG. 5) positions, it is necessary to constrain rotation of the inner sheath 22 to 180° by means of a stopping mechanism at both the open and closed positions. Similar to the sliding actuator button 48, two magnets 78A, 78B reside in the proximal face of the enlarged annular portion 62B of the sun gear 62. A third magnet 80 is supported at a distal end of the handle assembly 16. Magnet 80 maintains the sun gear 62 in one of two positions, depending on which one of the magnets 78A, 78B it is aligned with. As previously described, since the sun gear 62 rotates the inner sheath 22 connected to the cage gripper 30, the cage gripper is held in either its closed or open position in that manner.

This planetary gear system of the meshing gear knob 60B and sun gear 66 provides a gear reduction ratio that is designed so that a smaller turn of the knob 60 creates a relatively large turn of the sun gear 62. That way, a user does not have to turn the knob 60 180° to turn the cage gripper 30 180°. This is an ergonomic advantage—less rotation of the knob 60 means less range of motion, which means the thumb undergoes less stress. Also, the user does not have to adjust his/her hand grip half way through rotation of the knob 60. Instead, the thumb only needs to move through an arc of about 75° in the transverse plane.

Furthermore, utilizing the magnets 78A, 78B and 80 for stops imparts a very smooth feel for transitioning the cage gripper 30 from the open or un-deployed to the closed or deployed position. Like the actuator button 48, it requires the user to do nothing more than rotate the knob 60 to move the cage assembly 20 between the two positions.

As previously discussed, the cage housing 32 is connected to the outer sheath 24 while the cage gripper 30 is connected to the inner sheath. The cage assembly 20 has two positions: open and closed. In the open position (FIG. 3), the cage gripper 30 is rotated in such a way that it is completely housed or un-deployed inside the cage housing 32. This is the position at the beginning of a surgical procedure, before the lead 12 is attached to the bridge 28 and gripped by the cage assembly (FIG. 20).

Figure 17A:
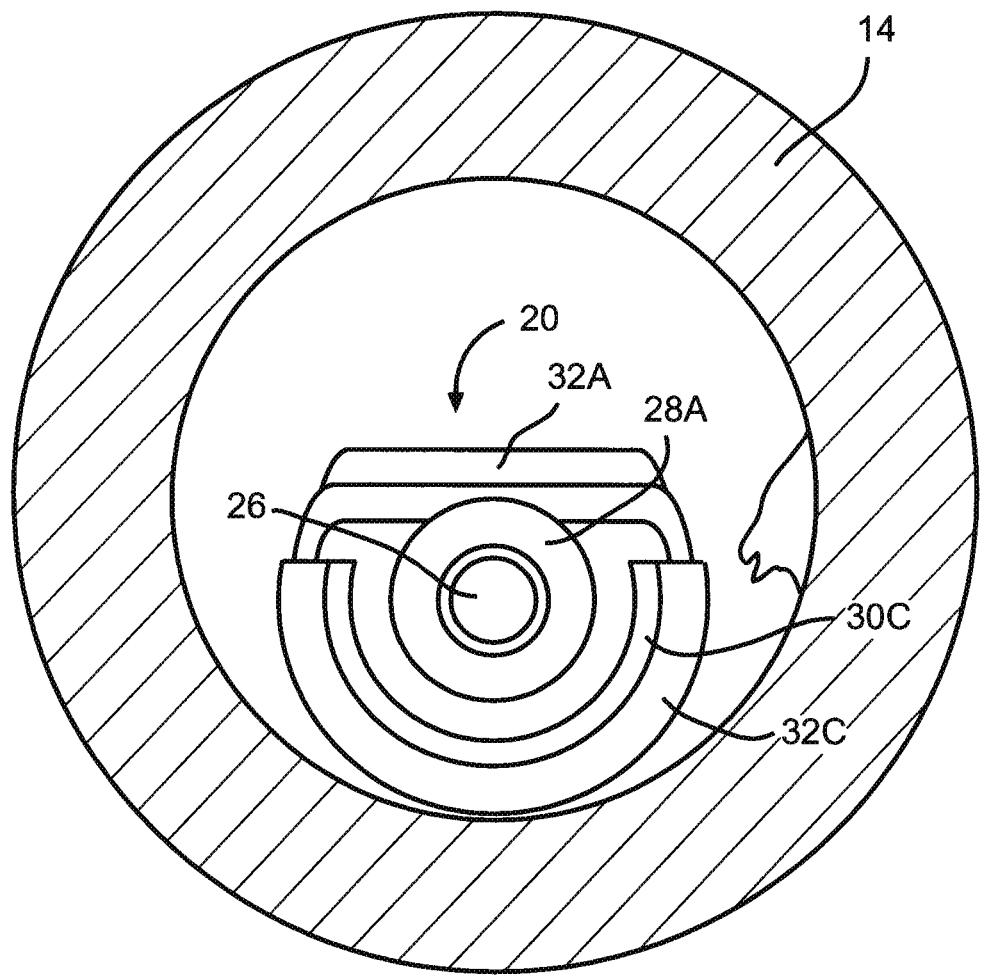
FIG. 17A is an end view of the cage assembly 20 shown in FIG. 10 in the vasculature 14.
Figure 18:
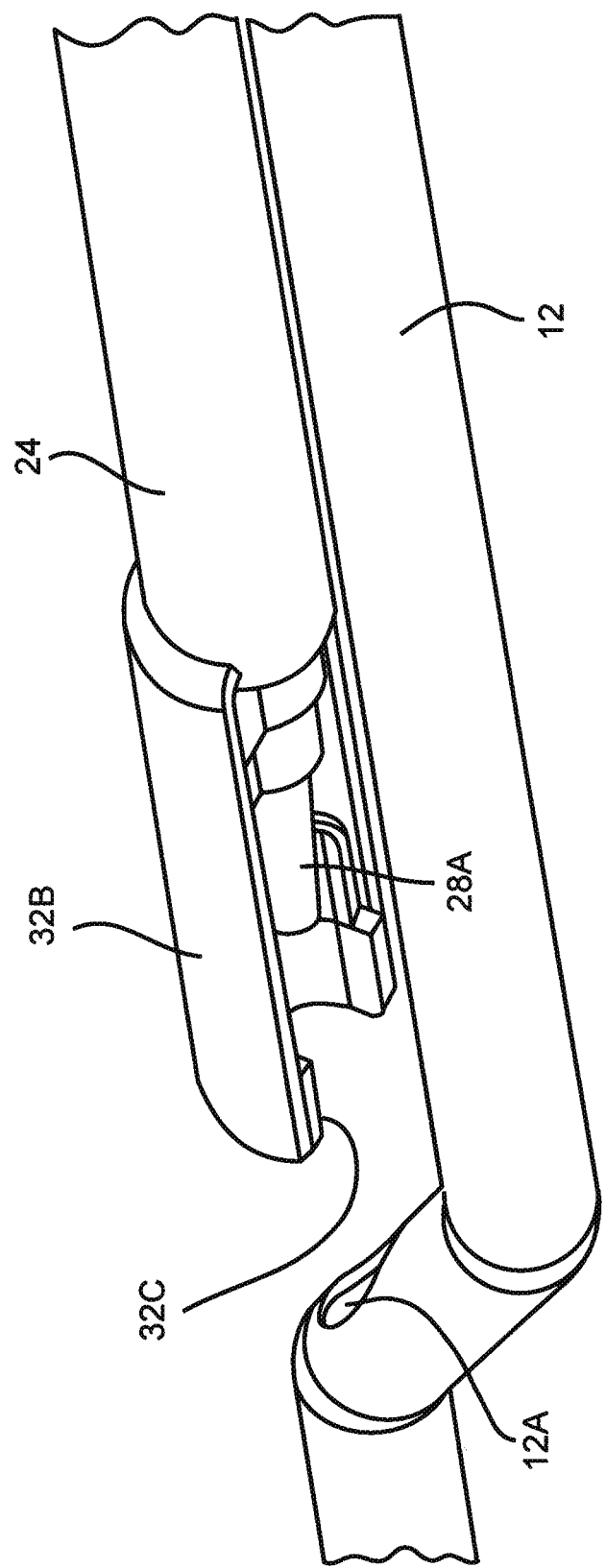
FIG. 18 is a perspective view showing the cage assembly 20 just prior to engagement of the tubing bridge 28 with a lead 12.

FIGS. 17 and 17A illustrate that the present catheter 10 has a relatively low profile that makes navigation of the cage assembly 20 through the vasculature, such as the super vena cava, relatively easy and atraumatic. In fact, the case assembly 20 provides a low profile without sharp edges or corners that could potentially damage or puncture the endothelial layer of the intima of a vessel.

At the beginning of a surgical procedure (FIG. 18), the lead 12 is slid into the cage housing 32 until the bridge 28 engages with an opening 12A in the lead (FIG. 19). This engagement provides communication through the bridge 28 and into a lumen (not shown) in the lead 12. Next, as previously discussed, the knob 60 on the housing assembly 16 is manipulated to rotate the cage gripper 30 180° into the closed position (FIG. 20) producing the deployed cage assembly position shown in FIG. 5. In that manner, the bridge 28 acts as a portion of the conduit for delivering a stylet (not shown) from the proximal end 16B of the handle assembly 16 located outside the body during the procedure to the lead lumen. The tip of the stylet has a small hex bit which functions to screw the lead anchoring helix (not shown) into the myocardium. At the end of the procedure, after the lead tip has been anchored, the cage gripper 30 is rotated back to the initial, open position shown in FIG. 3 and catheter 10 including the bridge 28 is withdrawn from the lead 12.

One potential issue that can arise clinically is that while the cage assembly 20 is in the closed position (FIGS. 5 and 20), the cage housing 32 or outer sheath 24 can become constrained while the cage gripper 39 and inner sheath 22 remain free to rotate. If either the handle 16 or outer sheath 24 is rotated at this point, the cage gripper 30 can unintentionally rotate in relation to the cage housing 32. If the cage gripper 30 rotates too far (over-rotates) in one direction, the cage gripper finger 30C can "cut" into the lead body 12. If the cage gripper 30 rotates too far in the other direction (under-rotates), a small opening is created between the gripper finger 30C and the partially cylindrically-shaped portion 32B of the cage housing 32. In the partially closed configuration, the lead 12 can inadvertently release or dislodge from the cage assembly 20.

Figure 21:
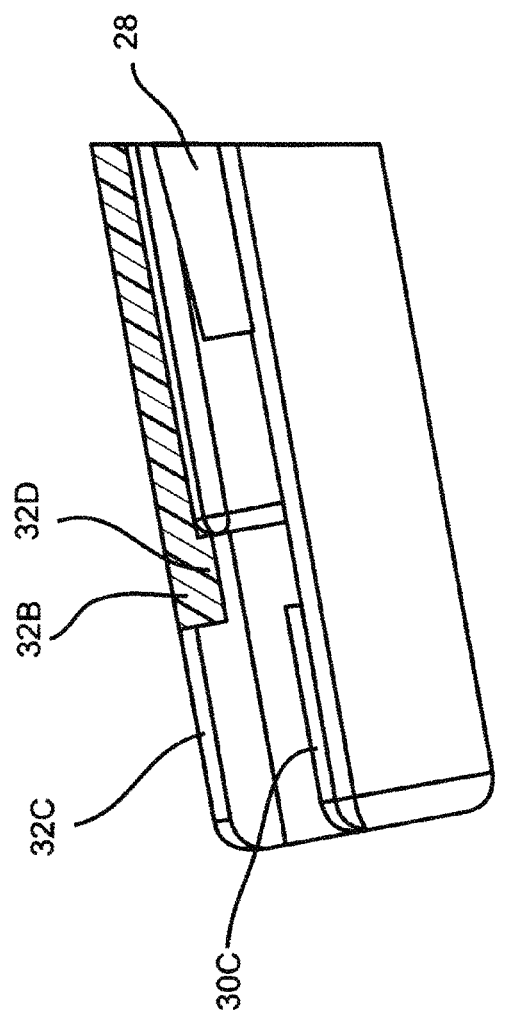
FIG. 21 is a perspective view, partly in cross-section, showing a rotation stop 32D of the cage housing 30 to prevent over rotation of the gripper finger 30C.

As illustrated in FIG. 21, one consideration is not to allow the cage gripper 30 to be over-rotated greater than 180° past the fully deployed position shown in FIG. 5. Such over deployment is prevented by having the leading edge of the gripper finger 30C contact a rotation stop 32D as a ledge provided into the thickness of the wall forming the partially cylindrical portion 32B of the cage housing 32. The amount of rotation by the cage gripper 30 does not necessarily have to be 180°. Instead, this angle could be tweaked by adjusting the depth of the rotation stop 32D in the cage housing 32. The stop could also be located in the cage housing 32 to prevent the cage gripper 30 from being rotated too much past the un-deployed position shown in FIG. 3.

A potential solution to under-rotation of the cage gripper 30 is to "over torque" the inner sheath 22 connecting between the knob 60 in the handle 16 and the cage gripper. This requires that the knob 60 be capable of rotating the proximal portion of the inner sheath 22 more than 180°. That is while the cage gripper 30 is kept from over-torquing (stopped at 180°) by the rotation stop 32D described above with respect to FIG. 21. In order to accomplish this, the gear ratio between the knob ring gear 60C and the sun gear 62 has to be set such that, for example, a 180° turn of the knob 60 in the closing direction (FIG. 5) actually rotates the sun gear 62 and the inner sheath 22 more than 180°. For example, the inner sheath 22 gets rotated 270°. This "over torque" of the inner sheath 22 serves to store up "closing torque" (i.e., potential energy), that keeps the cage gripper 30 in its closed position, even in those scenarios that previously caused under-rotated of the cage gripper 30.

In another embodiment, the knob 60 could directly rotate the inner sheath 22 thereby eliminating the planetary gear configuration of the gear knob 60B meshed with the sun gear 62.

When assembling the present catheter 10, it is important to ensure that the tip of the bridge 28 falls within the clasping area in relation to cage gripper 30. This location is a function of many variables, including the length of the outer sheath 22, the length of the inner sheath 24 and the length of the distal bridge 28, among other length considerations. When the tolerance stack up is calculated, it is very difficult to have an assembly in which the tip of the bridge 28 falls in the desired position, especially within a reasonable tolerance window.

A solution is to design some adjustability into the handle 16, such that the tip 28A of the distal bridge 28 can be set at a specific location during assembly, regardless of the tolerance stack up of all of the other components. One embodiment for accomplishing this is to design a movable nest 82 inside the housing 16 that allows the proximal location of the tab 72 overmolded onto the proximal end of the outer sheath 24 to be adjusted with respect to the position of the inner sheath 22. Assuming the distal bridge 28 secured to the inner sheath 22 is held constant, its distal tip 28A position will change in relation to the cage gripper 30 and cage housing 32 by providing the nest 72 as a longitudinally movable member housed inside the handle 16.

Figure 22:
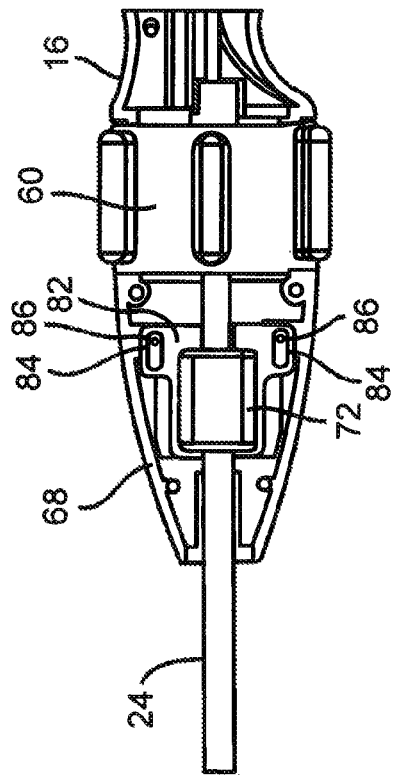
FIG. 22 is a side cross-sectional view showing a movable nest 82 housed inside the handle 16 and secured to the outer sheath 24.
Figure 23:
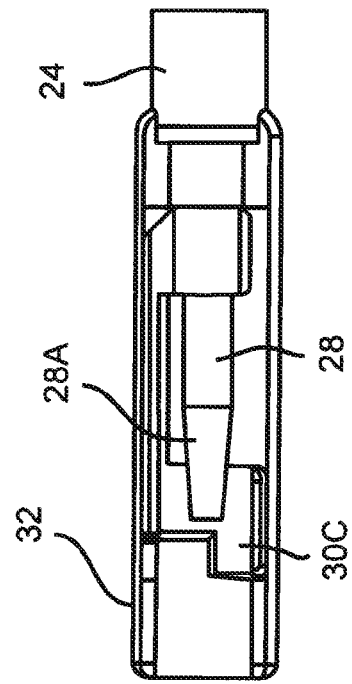
FIG. 23 is a cross-sectional view showing the relative position of the tubing bridge 28 and the gripper finger 30C as a result of the positioning of the nest 82 in FIG. 22.
Figure 24:
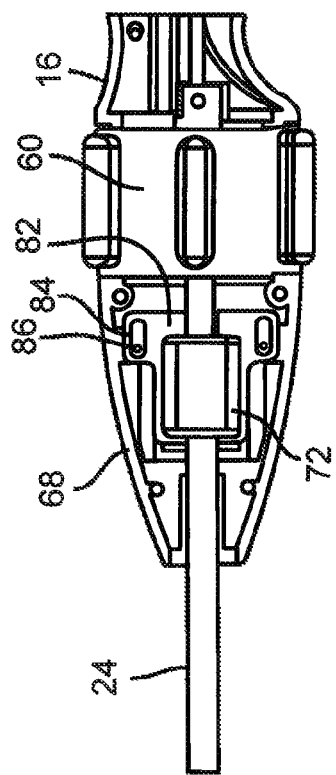
FIG. 24 is a side cross-sectional view of the movable nest 82 having been moved in a proximal direction with respect to the view shown in FIG. 23.
Figure 25:
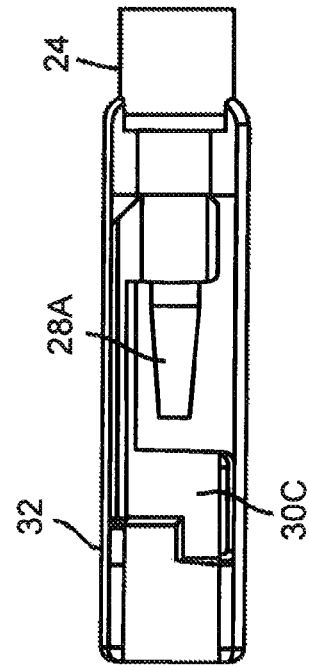
FIG. 25 is a cross-sectional view showing the relative position of the tubing bridge 28 and the gripper finger 30C as a result of the positioning of the nest 82 in FIG. 24.

As shown in FIGS. 22 and 24, the nest 82 supporting the overmolded tab 72 at the proximal end of the outer sheath 24 comprises spaced apart oval-shaped openings 84 supported on stationary pins 86 secured inside the handle 16. In FIG. 22, the nest 82 is at its distal most position with the pins 86 residing at the proximal end of the oval openings 84. This puts the distal bridge 28 in a position axially aligned with the cage finger 30C (FIG. 23). In FIG. 24, the movable nest 82 has been moved proximally with the pins 86 residing at the distal end of the openings 84. Now, the distal bridge 28 is in a position spaced proximally from the cage finger 30C. In that manner, the relative position of the cage housing 32 can be adjusted with respect to the gripper cage 30 and the distal bridge 28 during the manufacturing process.

It is appreciated that various modifications to the inventive concepts described herein may be apparent to those of ordinary skill in the art without departing from the spirit and scope of the present invention as defined by the appended claims.

What is claimed is:

1. A catheter, which comprises:
    a) a handle;

b) an inner sheath providing an inner sheath lumen extending along a first length from a proximal inner sheath portion supported by the handle to a distal inner sheath portion;

c) a cage gripper comprising a cage gripper sidewall providing a cage gripper lumen extending from a proximal cage gripper portion to a distal cage gripper portion having a distal cage gripper open end, wherein the proximal cage gripper portion is connected to the distal inner sheath portion to provide communication along the cage gripper lumen to the inner sheath lumen, and wherein the cage gripper sidewall has a first lateral opening providing lateral access to the cage gripper lumen and the distal cage gripper open end at a longitudinal axis of the cage gripper;

d) an outer sheath providing an outer sheath lumen extending along a second length from a proximal outer sheath portion supported by the handle to a distal outer sheath portion; and e) a cage housing comprising a cage housing sidewall providing a cage housing lumen extending from a proximal cage housing portion to a distal cage housing portion having a distal cage housing open end, wherein the proximal cage housing portion is connected to the distal outer sheath portion to provide communication along the cage housing lumen to the outer sheath lumen, and wherein the cage housing has a second lateral opening providing lateral access to the cage housing lumen and the distal cage housing open end at the longitudinal axis, f) wherein at least a portion of the inner sheath rotatably resides inside the outer sheath lumen with the cage gripper rotatably housed inside the cage housing lumen, and g) wherein the inner sheath is rotatably manipulatable to move the connected cage gripper into an open position with respect to the cage housing connected to the outer sheath to thereby align the first lateral opening with the second lateral opening such that there is open access through the second lateral opening of the cage housing into the first lateral opening of the cage gripper and then to the inner sheath lumen from the proximal inner sheath portion to the distal cage gripper and distal cage housing open ends at the longitudinal axis, and h) wherein the inner sheath is rotatably manipulatable to move the connected cage gripper into a closed position with respect to the cage housing to cause an annularly extending gripper finger portion of the cage gripper sidewall to at least partially close open access of the second lateral opening of the cage housing into the first lateral opening of the cage gripper, but with the distal cage gripper open end remaining coaxially aligned with the distal cage housing open end to continue providing open communication along the inner sheath lumen from the proximal inner sheath portion to the distal cage gripper and distal cage housing open ends at the longitudinal axis.

2. The catheter of claim 1 wherein the handle provides a handle lumen in open communication with the inner sheath lumen.

3. The catheter of claim 1 wherein the housing supports a first gear means connected to the inner sheath, the first gear means being manipulatable to rotate the inner sheath inside the outer sheath to consequently rotate the cage gripper inside the cage housing between the closed position to the open position.

4. The catheter of claim 1 wherein the handle supports the first gear means comprising a rotatable gear knob that meshes with a sun gear connected to the proximal inner sheath portion for selectively rotating the inner sheath inside the outer sheath.

5. The catheter of claim 4 wherein the sun gear supports spaced apart first and second magnets that are selectively attractable to a third magnet supported by the handle to thereby maintain the cage gripper connected to the inner sheath in either the open or the closed position.

6. The catheter of claim 4 wherein the gear knob and the sun gear provide a gear ratio such that angular manipulation of the gear knob produces a greater angular movement of the sun gear.

7. The catheter of claim 1 wherein the handle supports a valve that is in communication with the handle lumen and the inner sheath lumen.

8. The catheter of claim 7 wherein the handle supports an actuator button connected to a flexible tubing portion of the handle and inner sheath lumens and wherein the actuator button is movable longitudinally along the handle from a first position in which the flexible tubing is relatively straight for unobstructed communication from the valve and the handle lumen and into the inner sheath lumen to a second position in which the flexible tubing is kinked to thereby block unobstructed communication through the handle lumen and into the inner sheath lumen.

9. The catheter of claim 8 wherein the first position of the actuator button is proximal the second position.

10. The catheter of claim 8 wherein the actuator button supports spaced apart fourth and fifth magnets that are selectively attractable to a sixth magnet supported by the handle to thereby maintain the flexible tubing connected to the actuator button in either the straight or the kinked configuration.

11. The catheter of claim 1 wherein the distal inner sheath portion provides a distal bridge that is connectable to a lead.

12. The catheter of claim 11 wherein the distal bridge is at a position that is distal to where the inner sheath connects to the cage gripper.

13. The catheter of claim 1 wherein the inner and outer sheaths are flexible but substantially non-compressible along their respective first and second lengths.

14. The catheter of claim 5 wherein the first and second magnets are 180° apart.

15. The catheter of claim 14 wherein depending on which one of the first and second magnets is magnetically aligned with the third magnet supported by the handle provides the cage gripper being in either a closed or open position with respect to the cage housing.

16. A catheter, which comprises:

a) a handle supporting a first magnet;

b) a rotatable knob supported by the handle, wherein the rotatable knob supports a first gear;

c) an inner sheath providing an inner sheath lumen extending from a proximal inner sheath portion supported by the handle to a distal inner sheath portion;

d) a sun gear supported on the proximal inner sheath portion and in a geared engagement with the first gear, wherein the sun gear supports second and third spaced apart magnets facing the first magnet;

e) a cage gripper comprising a cage gripper sidewall providing a cage gripper lumen extending from a proximal cage gripper portion to a distal cage gripper portion having a distal cage gripper open end, wherein the proximal cage gripper portion is connected to the distal inner sheath portion to provide communication along the cage gripper lumen to the inner sheath lumen, and wherein the cage gripper sidewall has a first lateral opening providing lateral access to the cage gripper lumen and the distal cage gripper open end at a longitudinal axis of the cage gripper;

f) an outer sheath providing an outer sheath lumen extending from a proximal outer sheath portion supported by the handle to a distal outer sheath portion; and g) a cage housing comprising a cage housing sidewall providing a cage housing lumen extending from a proximal cage housing portion to a distal cage housing portion having a distal cage housing open end, wherein the proximal cage housing portion is connected to the distal outer sheath portion to provide communication along the cage housing lumen to the outer sheath lumen, and wherein the cage housing has a second lateral opening providing lateral access to the cage housing lumen and the distal cage housing open end at the longitudinal axis, h) wherein at least a portion of the inner sheath rotatably resides inside the outer sheath lumen with the cage gripper rotatably housed inside the cage housing lumen, and i) wherein the rotatable knob supported by the handle is manipulatable to cause rotational movement of the first gear in the geared engagement with the sun gear between an open position to a closed position, j) wherein in the open position the first lateral opening of the cage gripper is aligned with the second lateral opening of the cage housing such that there is open access through the second lateral opening into the first lateral opening and then to the inner sheath lumen from the proximal inner sheath portion to the distal cage gripper and distal cage housing open ends at the longitudinal axis, and wherein in the open position the first magnet supported by the housing is aligned with the second magnet of the sun gear to help maintain the cage gripper and the cage housing in the open position, and k) wherein in the closed position an annularly extending gripper finger portion of the cage gripper sidewall at least partially closes open access of the second lateral opening of the cage housing into the first lateral opening of the cage gripper, but with the distal cage gripper open end remaining coaxially aligned with the distal cage housing open end to continue providing open communication along the inner sheath lumen from the proximal inner sheath portion to the distal cage gripper and distal cage housing open ends at the longitudinal axis, and wherein in the closed position the first magnet supported by the housing is aligned with the third magnet of the sun gear to help maintain the cage gripper and the cage housing in the closed position.

17. The catheter of claim 16 wherein the handle supports a valve that is in communication with the handle lumen and the inner sheath lumen, and wherein the handle supports an actuator button connected to a flexible tubing portion of the handle and inner sheath lumens and wherein the actuator button is movable longitudinally along the handle from a first position in which the flexible tubing is relatively straight for unobstructed communication from the valve and the handle lumen and into the inner sheath lumen to a second position in which the flexible tubing is kinked to thereby block unobstructed communication through the handle lumen and into the inner sheath lumen.

18. The catheter of claim 17 wherein the first position of the actuator button is proximal the second position.

19. The catheter of claim 17 wherein the actuator button supports spaced apart fourth and fifth magnets that are selectively attractable to a sixth magnet supported by the handle to thereby maintain the flexible tubing connected to the actuator button in either the straight or the kinked configuration.

20. The catheter of claim 16 wherein the distal inner sheath portion provides a distal bridge that is connectable to a lead.

\* \* \* \* \*